(12) United States Patent
Hoyt et al.

(10) Patent No.: US 10,493,194 B2
(45) Date of Patent: Dec. 3, 2019

(54) AUTOMATED DEVICE FOR POINT-OF-CARE CELL PROCESSING

(71) Applicant: SpineSmith Partners, L.P., Austin, TX (US)

(72) Inventors: Joshua K. Hoyt, Portland, OR (US);
Greg Hinzmann, Beaverton, OR (US);
Paul DeKoning, Portland, OR (US);
David John Sayler, Portland, OR (US);
Theodore Sand, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 268 days.

(21) Appl. No.: 14/061,623

(22) Filed: Oct. 23, 2013

(65) Prior Publication Data

US 2014/0110317 A1 Apr. 24, 2014

Related U.S. Application Data

(60) Provisional application No. 61/717,473, filed on Oct. 23, 2012.

(51) Int. Cl.
*A61M 1/34* (2006.01)
*B01D 63/02* (2006.01)
*A61M 1/02* (2006.01)

(52) U.S. Cl.
CPC ............ *A61M 1/34* (2013.01); *A61M 1/0272* (2013.01); *A61M 1/0281* (2013.01); *B01D 63/02* (2013.01)

(58) Field of Classification Search
CPC ....................................................... A61M 1/34
See application file for complete search history.

(56) References Cited

U.S. PATENT DOCUMENTS

| | | | | |
|---|---|---|---|---|
| 4,475,666 A | * | 10/1984 | Bilbrey | B01L 3/021 222/14 |
| 4,706,207 A | * | 11/1987 | Hennessy | G01N 15/12 356/39 |
| 5,273,187 A | * | 12/1993 | Suzuki | B01L 3/0293 116/110 |
| 5,674,394 A | * | 10/1997 | Whitmore | A61M 1/3496 210/321.6 |
| 6,010,627 A | * | 1/2000 | Hood, III | A61K 35/14 210/321.6 |
| 6,143,252 A | * | 11/2000 | Haxo, Jr. | B01J 19/0046 422/131 |
| 6,348,156 B1 | * | 2/2002 | Vishnoi | A61M 1/3496 210/103 |
| 2002/0148282 A1 | * | 10/2002 | Hajduk | G01N 11/06 73/54.07 |
| 2003/0031590 A1 | * | 2/2003 | Park | A61M 1/3663 422/44 |

(Continued)

*Primary Examiner* — Matthew D Krcha
(74) *Attorney, Agent, or Firm* — Winstead PC

(57) ABSTRACT

The invention is directed to a device for the concentration of fluids comprising a donor receptacle containing a fluid to be concentrated, the donor receptacle comprising a plunger; a receiving receptacle to receive the concentrated fluid, the receiving receptacle comprising a plunger; a concentrator device that is connected to the donor receptacle and the receiving receptacle; and a housing that encloses the donor and receiving receptacles and the concentrator device that the plungers of the donor and receiving receptacles are enclosed within chambers that are gas tight.

8 Claims, 1 Drawing Sheet

(56) References Cited

U.S. PATENT DOCUMENTS

| | | | |
|---|---|---|---|
| 2004/0182788 A1* | 9/2004 | Dorian | B01D 15/02 210/649 |
| 2005/0029308 A1* | 2/2005 | Benett | B01L 3/0217 222/389 |
| 2005/0205498 A1* | 9/2005 | Sowemimo-Coker | A61K 35/15 210/782 |

* cited by examiner

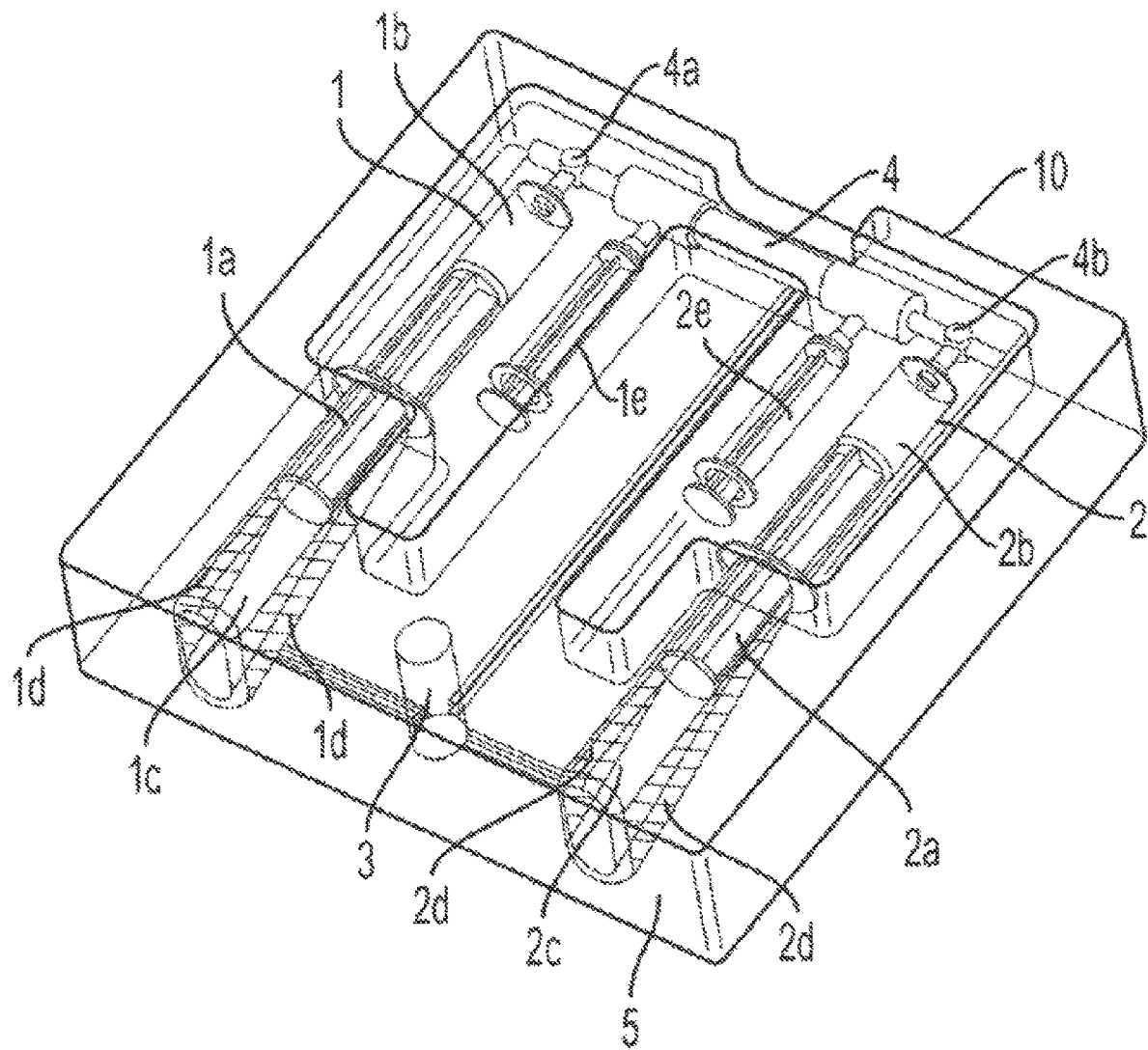

AUTOMATED DEVICE FOR POINT-OF-CARE CELL PROCESSING

CROSS-REFERENCES TO RELATED APPLICATIONS

This Application claims the benefit under 35 U.S.C. § 119(e) of U.S. Provisional Patent Application No. 61/717,473 filed Oct. 23, 2012 which is incorporated herein by reference in its entirety as if fully set forth herein.

BACKGROUND OF THE INVENTION

Platelet Rich Plasma (PRP) and Platelet Poor Plasma (PPP) derived from autologous blood/BMA samples are well understood products generated for use in treating humans. The concentration of various growth factors and proteins with a potential therapeutic benefit in PRP and PPP reflects that found in the plasma or bone marrow. There are advantages to having a concentrated form of PRP ("PRPC") and PPP ("PPC") when used for the formation of clots in treating various pathologies. One approach to creating these products uses pressure as the motive force for driving PRP or PPP (segregated from blood/BMA via centrifugation) through a filter constructed of hollow fibers. Due to the relatively small sample volumes and the need for low-cost single-use disposables, the hollow fiber filter system uses standard syringes to inject the sample and to extract the products. The processing of PPP or PRP in the hollow fiber device requires repetitive motions that can fatigue the operator. Consequently, there is a need for an automated system for use with generating PPC and PRPC.

Manual methods for pumping PPP or PRP through a hollow fiber device involve pressing on a syringe plunger to force fluid from the syringe through the hollow fiber "bed" with enough force to create a pressure gradient that "pushes" water out of the fluid and through the walls of the hollow fibers, thereby "dewatering" the fluid, since proteins and some growth factors are not able to pass through the pores of the hollow fibers. The effort to "pump" fluid from one syringe to the other, while maintaining sufficient force to efficiently "dewater" the fluid is laborious and cumbersome. The inventive device replaces the need for the operator to pump the fluid in the system manually, since the pneumatic mechanism will push the plungers in sequence to force the fluid from one syringe to the other. The existing disposable device design and operating principle remains the same so there is no change in the disposable device in order to utilize the inventive device. Appropriate controls will be built into the device in order to provide additional control for concentrating the PPP or PRP (or other therapeutic fluids).

SUMMARY OF THE INVENTION

The invention is directed to a device for the concentration of fluids comprising a donor receptacle containing a fluid to be concentrated, the donor receptacle comprising a plunger; a receiving receptacle to receive the concentrated fluid, the receiving receptacle comprising a plunger; a concentrator device that is connected to the donor receptacle and the receiving receptacle; and a housing that encloses the donor and receiving receptacles and the concentrator device that the plungers of the donor and receiving receptacles are enclosed within chambers that are gas tight.

BRIEF DESCRIPTION OF THE DRAWINGS

FIG. 1 shows a device for the concentration of therapeutic fluids in accordance with an embodiment of the invention.

DESCRIPTION OF EXEMPLARY EMBODIMENTS OF THE INVENTION

An embodiment of the invention is directed to a device for the concentration of fluids comprising: a donor receptacle containing a fluid to be concentrated, the donor receptacle comprising a plunger; a receiving receptacle to receive the concentrated fluid, the receiving receptacle comprising a plunger; a concentrator device that is connected to the donor receptacle and the receiving receptacle; and a housing that encloses the donor and receiving receptacles and the concentrator device that the plungers of the donor and receiving receptacles are enclosed within chambers that are gas tight. In an embodiment of the device, the plungers of the receptacles move in a coordinated manner through the use of pneumatic force such that the insertion of a plunger within its receptacle causes the other plunger to advance out of its receptacle.

In certain embodiments, the donor receptacle and the receiving receptacle of the device are syringes. In other embodiments, the concentrator device is a hollow fiber concentrator device. In certain embodiments, the pneumatic force applied in the chambers is controlled by an electronic controller.

In certain embodiments of the invention, the donor receptacle and receiving receptacle are engaged in a continuous process whereby multiple cycles/rounds of concentration of therapeutic fluid can be achieved. In certain embodiments, the number of cycles/rounds is recorded and displayed. In certain embodiments of the invention, the distance advanced by the plungers is determined by a sensor array aligned along the chamber walls of the housing surrounding the donor and receiving receptacles.

An embodiment of a concentration device is shown in FIG. 1. The device 10 comprises a donor receptacle 1 and a receiving receptacle 2. The donor receptacle 1 comprises a plunger 1 *a* and the receiving receptacle 2 comprises a plunger 2 *a*. The donor receptacle 1 comprises a chamber 1 *b* within which the donor receptacle plunger 1 *a* is housed. Similarly, the receiving receptacle 2 comprises a chamber 2 *b* within which the receiving receptacle plunger 2 *a* is housed. The device 10 also includes a gas-tight chamber 1 *c* that houses the donor receptacle 1 and a gas-tight chamber 2 *c* that houses the receiving receptacle 1. A concentrator 4 is located between the donor receptacle 1 and the receiving receptacle 2. The concentrator 4 is connected to each of the donor receptacle 1 and the receiving receptacle 2 via connectors 4 *a* and 4 *b* respectively. In certain embodiments of the invention, the concentrator 4 is a hollow fiber concentrating device. In other embodiments of the invention, donor receptacle 1 and the receiving receptacle 2 are syringes.

During operation of the device 10, the donor receptacle 1 is filled with a therapeutic fluid such as PPP or PRP. The therapeutic fluid fills the chamber 1*b* of the donor receptacle 1. After the chamber 1*b* is filled with the fluid that is to be concentrated, donor receptacle 1 and receiving receptacle 2 are placed into gas-tight chambers 1 *c*, 2 *c*, respectively, as illustrated in FIG. 1. Pneumatic force is applied to gas-tight chamber 1 *c* and the donor receptacle plunger 1 *a* is pushed such that compressive force is exerted on the plunger 1 *a*, which in turn causes the therapeutic fluid that is present in chamber 1 *b* to move through connector 4 *a* into the concentrator 4. The continued application of compressive force on the plunger 1 *a* causes the therapeutic fluid to move through the connector and into the receiving receptacle 2 via connector 4 *b*. After the therapeutic fluid has been transferred into the chamber 2 *b* of the receiving receptacle 2, the pneumatic pressure being applied to plunger 1 *a* is turned off and the pneumatic pressure is switched via a valve 3 to the gas-tight chamber 2 *c* that houses the receiving receptacle 2. When compressive pressure is applied to plunger 2 *a* via the pneumatic force, the therapeutic fluid within chamber 2 *b* of the receiving receptacle 2 is pushed into the concentrator 4 via connector 4 *b*, and into chamber 1 *b* of the donor receptacle 1. Thus, using a pattern of pneumatic pressure cycles, the therapeutic fluid is moved back and forth from the donor receptacle 1 to the receiving receptacle 2 through the concentrator 4, which results in the concentration of the therapeutic fluid.

The gas-tight chambers 1 *c*, 2 *c* are lined with an array of sensors 1 *d* and 2 *d*, respectively. The sensors 1 *d* and 2 *d* track the movement of the plungers 1 *a* and 2 *a*, respectively, and their reduced displacement as the therapeutic fluid becomes more concentrated. Since the process of concentrating the therapeutic fluid entails removal of water from the fluid, dewatering syringes 1 *e* and 2 *e* are connected to the concentrator in order to remove any fluid buildup during the concentration sequence.

An embodiment of the invention provides an automated process for the concentration of therapeutic fluids like PRP and PPP. The inventive device supplies the compressive force required to move the plunger in one syringe (already loaded with the therapeutic fluid to be concentrated) in order to displace the therapeutic fluid through the hollow fiber concentrating device and into a receiving syringe during the first cycle. The physical arrangement of the inventive device is shown in FIG. 1, with the required syringes and the hollow fiber device connected as would be required for concentrating therapeutic fluids. After the fluid is transferred through the hollow fiber device and into the receiving syringe, the pneumatic pressure is switched off in the first syringe chamber and switched via a valve to the chamber containing the receiving syringe in order to displace the fluid out of the receiving syringe back into the originating syringe. In this manner, the therapeutic fluid is moved during each pneumatic force cycle through the hollow fiber concentrating device and into the other syringe. Suitable detectors are arrayed along the path that each plunger follows during a filling step in order to track the displacement during each cycle. Since water is being lost during each cycle it is necessary to have a series of detectors in order to be able to sense the reduced displacement as the therapeutic fluid becomes more concentrated. One such detector is a source LED and a sensor capable of detecting the emitted light, such that as the plunger moves past the emitter/detector pair the light will be blocked and that will be "sensed" by the on-board electronics. An array of sensors is located along the walls of the pneumatic chambers that house respectively the donor syringe and the receiving syringe. In alternate embodiments, other configurations and detector strategies are possible.

While the foregoing description is intended to reflect a fully "automated" operation once the syringes and hollow fiber device are mounted in the inventive device, it is possible for a "semi-automated" operation to be performed, in which the operator physically activates the pneumatic force cycle and manually switches the value between the two syringe chambers in succession to recreate the "pumping" of the therapeutic fluid through the hollow fiber device.

The number of cycles of concentration may be predetermined based on the amount of therapeutic fluid to be concentrated and the controller programmed to perform that selected number of cycles or else the operator can monitor the extent of dewatering that has occurred after a certain number of cycles and assess whether or not to continue the concentrating sequence. A cycle "counter" will display the number of cycles to aid the operator in the enumeration of the number of cycles performed during a concentrating sequence.

At the end of the concentrating sequence, a valve will release any residual pressure in a syringe chamber after which the inventive device can be opened and the concentrated therapeutic fluid recovered for use in the patient. Dewatering syringes are present in order to remove any fluid buildup during the concentration sequence. These can be accessed by suspending the concentration cycling, de-pressurizing the syringe chambers and then opening the inventive device. Fluid from the dewatering compartment can be drawn off with the syringes in place without the need to remove the hollow fiber device, thereby maintaining sterility of the configuration.

Working Example

The tools and instrumentation (e.g., cannulae) for performing fluid-only sample collection will be transferred to the sterile field or other appropriate physical location near the patient. Once the patient's sample has been collected from an adipose tissue depot and loaded into the appropriate sterile, single-use fiber-containing device it is inserted into the processing platform on the work station in order to reduce the volume of the sample. Volume reduction can be obtained by activating the passage of fluid through the lumen of the fibers in the device via attached syringes, with an automated sequence involving pneumatic motion of the syringes after the syringes have been loaded into the pneumatic device. Water, ions and some biological materials will pass through the pores of the fibers, while cells, including white blood cells, red blood cells, platelets, neutrophils, mononuclear cells and progenitor cells, along with biologically relevant proteins and growth factors will be retained with the lumen of the fibers. Once volume reduction of the patient's sample has been achieved, the luminal compartment is accessed to recover the patient's therapeutic biological preparation. Once the final therapeutic cell-containing or biological fluid-containing therapeutic preparation has been obtained, the preparation is transferred under direction of the physician in a manner so as to enable treatment of the patient. Results of the cell concentration and viability of fluid-only patient samples after processing in a fiber-containing device is shown in Table 1. The cell analysis was performed with a NucleoCounter (Chemometec, Inc.) and consists of two cartridges being loaded with a small aliquot of the cell preparation, either before processing or after processing. As indicated, the change in viability of the samples processed in the fiber-containing device was less than 10%, indicating that the physical process of flow through the lumen of the fibers did not cause a substantial change in viability, despite the shear forces being experienced by the cells as they flow through the fibers. Table 1 shows the Cell viability after concentration through fiber-containing devices using platelet-rich plasma (PRP), bone marrow concentrate (BMC), or BMC with adipose tissue-derived Fluid-only cells (also called stromal vascular fraction [SVF] cells).

TABLE 1

| Sample ID | Cell Type | Initial Cell Concentration (TNC/mL) | Final Cell Concentration (TNC/mL) | Fold Increase in Cell Concentration | Change in Cell Viability after Concentration |
|---|---|---|---|---|---|
| 1 | PRP | $4.55 \times 10^7$ | $2.58 \times 10^8$ | 5.67 | −0.5% |
| 2 | BMC | $1.05 \times 10^6$ | $3.99 \times 10^6$ | 3.8 | −2.1% |
| 3 | BMC | $1.16 \times 10^7$ | $7.03 \times 10^7$ | 6.1 | +44.4% |
| 4 | BMC + SVF | $9.30 \times 10^5$ | $9.35 \times 10^6$ | 10.1 | +0.7% |

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. A device for concentrating fluids comprising:
    a disposable syringe donor receptacle containing a fluid to be concentrated, the disposable syringe donor receptacle comprising a donor plunger, the donor plunger comprising a first plunger head sealingly engaged with a receptacle of the disposable syringe donor receptacle;
    a disposable syringe receiving receptacle to receive the fluid to be concentrated from the disposable syringe donor receptacle, the disposable syringe receiving receptacle comprising a receiving plunger, the receiving plunger comprising a second plunger head sealingly engaged with a receptacle of the disposable syringe receiving receptacle;
    a concentrator device that is connected to the disposable syringe donor receptacle and the disposable syringe receiving receptacle;
    a housing comprising a first gas-tight chamber adapted to securely receive the donor plunger within the first gas-tight chamber and a second gas-tight chamber adapted to securely receive the receiving plunger within the second gas-tight chamber;
    an electronic controller configured to control movement of the donor plunger and the receiving plunger by directing a pressurized fluid into the first and second gas-tight chambers; and
    a valve coupled to the first and second gas-tight chambers to selectively direct the pressurized fluid to the donor plunger or the receiving plunger;
    wherein each of the first and second gas-tight chambers comprises a configuration that allows the pressurized fluid to contact a back side of the first and second plunger head, respectively, to cause the first and second plunger head to move in response to the pressurized fluid contacting the back side of the first and second plunger head.

2. The device of claim 1, wherein the concentrator device is a hollow fiber concentrator device.

3. The device of claim 1, further comprising a dewatering syringe disposed within the housing and coupled to the concentrator device.

4. The device of claim 1, further comprising a second dewatering syringe disposed within the housing and coupled to the concentrator device.

5. The device of claim 1, further comprising:
    a cycle counter coupled to the electronic controller; and
    wherein the electronic controller records a number of concentration cycles and displays the number of concentration cycles on the cycle counter.

6. The device of claim 1, wherein the electronic controller is programmed to perform a selected number of cycles.

7. The device of claim 1, further comprising a first sensor array aligned along a wall of the first gas-tight chamber and aligned adjacent to the donor plunger and a second sensor array disposed on a wall of the second gas-tight chamber and aligned adjacent to receiving plunger, wherein the first sensor array monitors a distance the donor plunger travels to track a reduced displacement of the donor plunger and the second sensor array monitors a distance the receiving plunger travels to track a reduced displacement of the receiving plunger.

8. The device of claim 7, wherein the first sensor array comprises:
    a light source; and
    a sensor positioned so that the donor plunger is between a light path of the light source and the sensor and capable of detecting light emitted from the light source such that, as the donor plunger moves between the light source and the sensor, the sensor detects movement of the donor plunger.

* * * * *